United States Patent
Nishimura et al.

(10) Patent No.: US 11,896,205 B2
(45) Date of Patent: Feb. 13, 2024

(54) DIGESTIVE ORGAN INTERNAL CONTENTS SAMPLING CAPSULE

(71) Applicant: Hitachi, Ltd., Tokyo (JP)

(72) Inventors: Ayako Nishimura, Tokyo (JP); Akihiko Kandori, Tokyo (JP); Tsukasa Funane, Tokyo (JP); Akiko Obata, Tokyo (JP); Hirokazu Atsumori, Tokyo (JP); Masashi Kiguchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 403 days.

(21) Appl. No.: 17/204,001

(22) Filed: Mar. 17, 2021

(65) Prior Publication Data
US 2022/0087655 A1   Mar. 24, 2022

(30) Foreign Application Priority Data

Sep. 18, 2020   (JP) .................................. 2020-157579

(51) Int. Cl.
*A61B 10/00* (2006.01)
*A61B 5/07* (2006.01)
(Continued)

(52) U.S. Cl.
CPC .......... *A61B 10/0045* (2013.01); *A61B 5/073* (2013.01); *A61B 5/6861* (2013.01);
(Continued)

(58) Field of Classification Search
CPC ... A61B 10/0045; A61B 5/073; A61B 5/6861; A61B 10/0038; A61B 5/6871;
(Continued)

(56) References Cited

U.S. PATENT DOCUMENTS

2004/0097834 A1   5/2004 Stoltz
2010/0145316 A1 * 6/2010 Mintchev .............. A61M 31/00
                                                     604/890.1
(Continued)

FOREIGN PATENT DOCUMENTS

JP      2004-529733 A    9/2004
JP       2005-80933 A    3/2005
(Continued)

OTHER PUBLICATIONS

Japanese-language Office Action issued in Japanese Application No. 2020-157579 dated Oct. 24, 2023 with English translation (10 pages).

*Primary Examiner* — Matthew Kremer
*Assistant Examiner* — Jonathan Drew Moroneso
(74) *Attorney, Agent, or Firm* — Crowell & Moring LLP

(57) ABSTRACT

A digestive organ internal contents sampling capsule for sampling internal contents in a digestive organ includes: a cylindrical container insoluble in a digestive tract for housing the internal contents in the digestive organ; an outer lid enclosing an orifice of the cylindrical container and to dissolve at least partially in the digestive organ; an inner lid arranged in the cylindrical container, and to swell in response to contact with the internal contents in the digestive organ to enclose the orifice of the cylindrical container after the orifice is exposed by dissolving of at least a part of the outer lid; and a marker material to be discharged together with the cylindrical container housing the internal contents in the digestive organ and feces.

14 Claims, 11 Drawing Sheets

(51) Int. Cl.
*A61B 5/00* (2006.01)
*A61M 31/00* (2006.01)

(52) U.S. Cl.
CPC ........ *A61B 10/0038* (2013.01); *A61B 5/6871* (2013.01); *A61B 2010/0061* (2013.01); *A61B 2560/0406* (2013.01); *A61B 2562/02* (2013.01); *A61B 2562/162* (2013.01); *A61M 31/00* (2013.01)

(58) Field of Classification Search
CPC .... A61B 2010/0061; A61B 2560/0406; A61B 2562/02; A61B 2562/162; A61M 31/00
See application file for complete search history.

(56) References Cited

U.S. PATENT DOCUMENTS

| | | |
|---|---|---|
| 2016/0038086 A1 | 2/2016 | Wrigglesworth et al. |
| 2017/0252016 A1* | 9/2017 | Wrigglesworth .. A61B 10/0045 |
| 2018/0168490 A1* | 6/2018 | Jones ................... A61B 5/7282 |
| 2019/0219553 A1* | 7/2019 | Duan ....................... A61J 3/07 |
| 2020/0138416 A1 | 5/2020 | Shalon |

FOREIGN PATENT DOCUMENTS

| | | |
|---|---|---|
| JP | 2019-150587 A | 9/2019 |
| WO | WO-2020214689 A1 * | 10/2020 |

* cited by examiner

DIGESTIVE ORGAN INTERNAL CONTENTS SAMPLING CAPSULE

CLAIM OF PRIORITY

The present application claims priority from Japanese patent application JP2020-157579 filed on Sep. 18, 2020, the content of which is hereby incorporated by reference into this application.

BACKGROUND

The present invention relates to a capsule for sampling internal contents in a digestive organ in the digestive organ of a living body.

Internal contents in a digestive organ of a digestive tract are available for testing the condition of this digestive organ. In particular, it has apparently been shown that intestinal bacterial flora reflecting an intestinal environment relates to many diseases, which shows the importance of testing the intestinal bacterial flora. A specimen of the intestinal bacterial flora is generally sampled from feces. However, feces are considered to be reflection of an environment in a large intestine, so that an intestinal environment in a small intestine playing important roles in immunity, absorption of nourishment, and metabolism is unknown.

An endoscope is used as a method of testing the interior of a small intestine. This test involves removal of internal contents in the small intestine, however, making it impossible to test an intestinal environment in the small intestine in a usual condition. Testing an accurate intestinal environment in the small intestine requires sampling of intestinal internal contents in a usual condition and acquiring information about the sampled internal contents. A method of acquiring internal contents in a small intestine is disclosed in Japanese Patent Application Publication No. 2019-150587 or Japanese Patent Application Publication (Translation of PCT Application) No. 2004-529733, for example.

SUMMARY OF INVENTION

As disclosed in the foregoing conventional techniques, a simple method of acquiring internal contents in a small intestine includes biochemical analysis as a final step. This requires recovery of a device from feces. However, the foregoing conventional techniques do not give consideration to recovering the device efficiently from feces. In this regard, a technique allowing sampling of internal contents in a small intestine using a sampling capsule and allowing efficiently recovering the used sampling capsule has been desired.

One aspect of the present invention is a digestive organ internal contents sampling capsule for sampling internal contents in a digestive organ including: a cylindrical container insoluble in a digestive tract for housing the internal contents in the digestive organ; an outer lid enclosing an orifice of the cylindrical container and to dissolve at least partially in the digestive organ; an inner lid arranged in the cylindrical container, and to swell in response to contact with the internal contents in the digestive organ to enclose the orifice of the cylindrical container after the orifice is exposed by dissolving of at least a part of the outer lid; and a marker material to be discharged together with the cylindrical container housing the internal contents in the digestive organ and feces.

The one aspect of the present invention allows sampling of internal contents in a digestive organ using the sampling capsule and allows the used sampling capsule to be recovered efficiently.

DETAILED DESCRIPTION OF THE EMBODIMENTS

Figure 1:
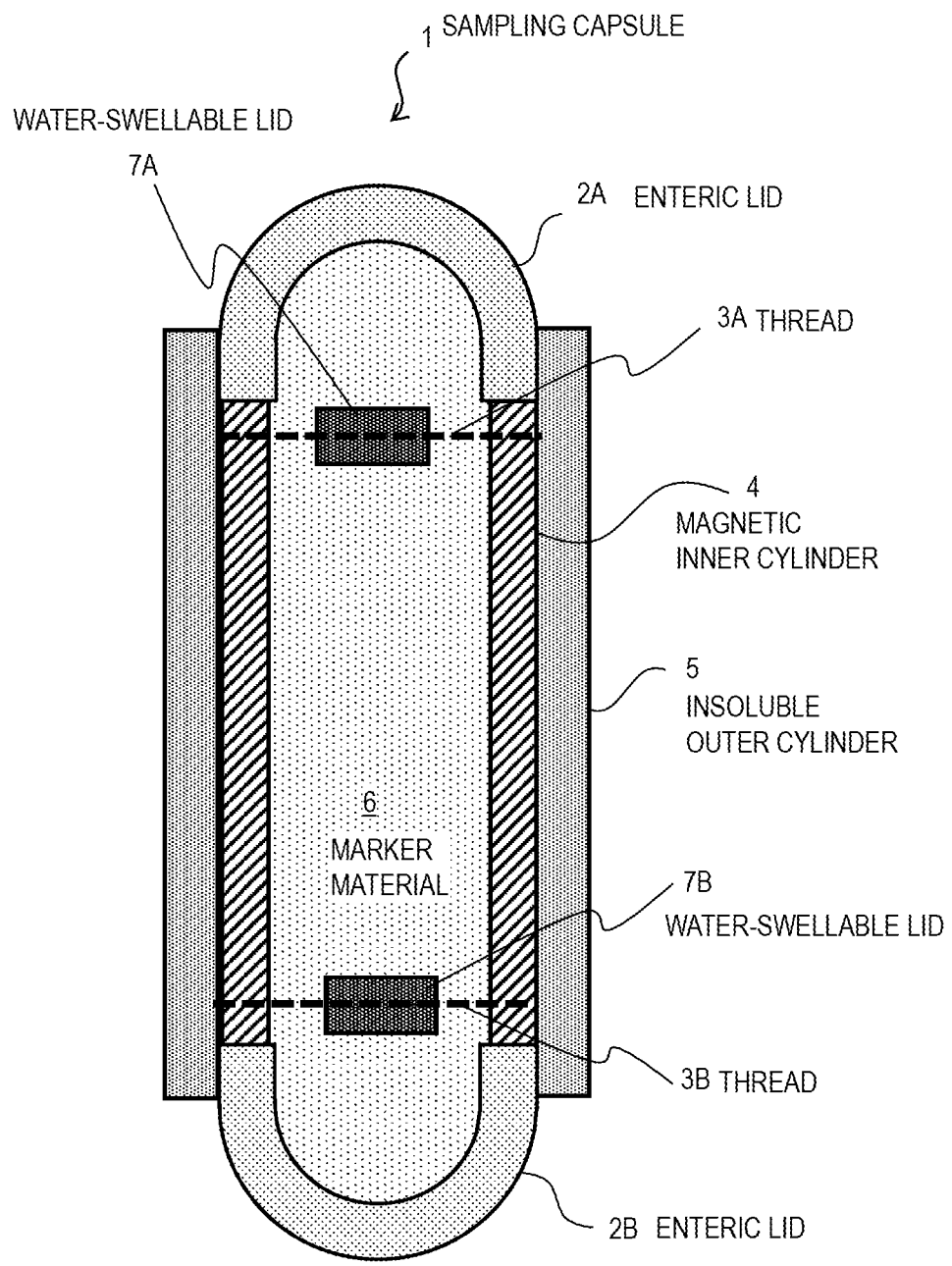
FIG. 1 shows an exemplary configuration of an intestinal internal contents sampling capsule for sampling internal contents in a small intestine according to a first embodiment.

Embodiments will be described in detail below by referring to the drawings. It should be noted that the following description is merely an example for realizing the present invention and is not intended to limit the technical scope of the present invention. A digestive organ internal contents sampling capsule described in the following embodiments is used for sampling internal contents in a digestive organ of a digestive tract.

Digestive organs of a digestive tract include a gastrointestine, the gastrointestine is a stomach or an intestine, and the intestine is a large intestine or a small intestine. The digestive organ internal contents sampling capsule is swallowed by a test subject, houses digestive organ internal contents, and is discharged together with feces. As this sampling capsule is a swallowable capsule, it allows digestive organ internal contents in a usual condition to be sampled without causing serious distress to the test subject.

In specification description, an exemplary configuration of the digestive organ internal contents sampling capsule includes a marker material showing the position of this sampling capsule in feces and facilitating discovery of this sampling capsule. The marker material is a constituting element of the sampling capsule and is discharged together with feces. For recovery of the sampling capsule discharged from a body, an area indicated by the marker in the feces can be used as a target for searching for the sampling capsule, thereby alleviating burden of recovering the sampling capsule.

According to one example, the marker material is housed in the sampling capsule and released in a digestive organ. The marker material is discharged in feces together with the sampling capsule. An area including the marker material exhibits a different condition from a surrounding usual area in terms of a different color, pattern, or texture, for example. By doing so, a tester becomes capable of easily estimating the position of the sampling capsule. The marker material is a food that may be a coloring matter such as melanin from squid ink or seeds, for example. This makes it possible to avoid influence on a test subject reliably.

According to a different exemplary configuration, the marker material is contained in a material of a fixed part of the digestive organ internal contents sampling capsule. For example, the marker material is a fluorescent material. The fluorescent material emits light in a specific color in response to light coming from outside such as an ultraviolet ray or visible light. For example, applying ultraviolet light to feces makes it possible to identify the position of the sampling capsule easily in the feces.

In the following, an intestinal internal contents sampling capsule for sampling internal contents in a small intestine will be described as each of the embodiments described below of this specification. Features of the embodiments described below are applicable to a sampling capsule for sampling internal contents in a digestive organ of a digestive tract differing from a small intestine such as internal contents in a stomach, for example.

First Embodiment

FIG. 1 shows an exemplary configuration of an intestinal internal contents sampling capsule (hereinafter also called a sampling capsule simply) for sampling internal contents in a small intestine according to an embodiment of this specification. FIG. 1 shows an exemplary configuration of an intestinal internal contents sampling capsule 1 before being swallowed and shows a sectional view taken along the axis of the sampling capsule 1. A vertical direction in FIG. 1 corresponds to the axis direction of the intestinal internal contents sampling capsule 1. The intestinal internal contents sampling capsule 1 includes an enteric lid 2A, an enteric lid 2B, a thread 3A, a thread 3B, a magnetic inner cylinder 4, an insoluble outer cylinder 5, a marker material 6, a water-swellable lid 7A, and a water-swellable lid 7B. The intestinal internal contents sampling capsule 1 may have a size with an entire length from about 17 to about 25 mm and an outer diameter from about 7 to 10 mm, for example.

The insoluble outer cylinder 5 is a cylindrical part made of a material insoluble in a digestive tract (digestive tract insoluble material). According to one example, the insoluble outer cylinder 5 may be made of an elastic material such as silicon, polyvinyl chloride (PVC), or polyethylene (PE).

According to the exemplary configuration shown in FIG. 1, the insoluble outer cylinder has a circular cylindrical shape and has a constant sectional shape as viewed along the axis thereof. The section of the insoluble outer cylinder 5 may have a shape differing from a circle such as a shape defined by a curve of an oval or defined by lines of a rectangle, for example. The insoluble outer cylinder 5 may have a varying sectional shape. According to the exemplary configuration shown in FIG. 1, both sides of the insoluble outer cylinder 5 are opened and orifices are formed on the both sides. According to a different exemplary configuration, one side of the insoluble outer cylinder 5 may be closed and an orifice (opening) may be formed only on the other side.

The insoluble outer cylinder 5 is an outer cylinder, and the magnetic inner cylinder 4 as an inner cylinder is arranged inside the outer cylinder. The insoluble outer cylinder 5 and the magnetic inner cylinder 4 form a cylindrical container. The magnetic inner cylinder 4 is made of a magnetic material insoluble in a digestive tract such as iron or stainless steel (SUS430, for example). The magnetic material is attracted to a magnet. Thus, using a magnet allows the intestinal internal contents sampling capsule 1 to be recovered easily from feces. The magnetic inner cylinder 4 may be made of a nonmagnetic material such as nonmagnetic metal or resin, for example.

According to the exemplary configuration shown in FIG. 1, the magnetic inner cylinder 4 is housed entirely in the insoluble outer cylinder 5, and at least a part of the outer surface of the magnetic inner cylinder 4 tightly contacts the inner surface of the insoluble outer cylinder 5. The insoluble outer cylinder 5 expanded by the magnetic inner cylinder 4 exerts elastic force (contractile force) to hold the insoluble outer cylinder 5 on the magnetic inner cylinder 4. By doing so, assembly of the intestinal internal contents sampling capsule is facilitated. A different holding method is also applicable.

As will be described later, a part can be fixed to the magnetic inner cylinder 4 and the insoluble outer cylinder 5 by interposing this part at least partially between the magnetic inner cylinder 4 and the insoluble outer cylinder 5. Surrounding the rigid magnetic inner cylinder 4 using the softer insoluble outer cylinder 5 makes it possible to avoid influence on a digestive tract more reliably. The magnetic inner cylinder 4 having higher rigidity allows the cylindrical container to be less prone to deformation.

According to the exemplary configuration shown in FIG. 1, the magnetic inner cylinder 4 has a circular cylindrical shape and has a constant sectional shape as viewed along the axis thereof. The magnetic inner cylinder 4 may have an inner diameter from about 6 to about 9 mm, for example. The section of the magnetic inner cylinder 4 may have a shape differing from a circle such as a shape defined by a curve of an oval or defined by lines of a rectangle, for example. The magnetic inner cylinder 4 may have a varying sectional shape.

According to the exemplary configuration shown in FIG. 1, both sides of the magnetic inner cylinder 4 are opened and orifices are formed on the both sides. This allows intestinal internal contents to flow effectively into the magnetic inner cylinder 4. According to a different exemplary configuration, like the insoluble outer cylinder 5, the magnetic inner cylinder 4 may be closed on one side and an orifice (opening) may be formed only on the other side. By doing so, the magnetic inner cylinder 4 and the insoluble outer cylinder 5 are opened on the same side. According to the exemplary configuration shown in FIG. 1, while the cylindrical container is composed of the magnetic inner cylinder 4 and the insoluble outer cylinder 5, one of these cylinders may be omitted or another cylinder may be added.

The orifices on the both sides of each of the magnetic inner cylinder 4 and the insoluble outer cylinder 5 are enclosed by corresponding ones of the enteric lids 2A and 2B each corresponding to an outer lid. The enteric lids 2A and 2B have the same shape and are made of the same material. The enteric lids 2A and 2B may have different shapes or may be made of different materials. The enteric lids 2A and 2B are made of an enteric material and may be made of hydroxypropylmethylcellulose, gelatin, carrageenan, starch, or agar, for example. These materials do not dissolve in a stomach but dissolve in a small intestine.

Figure 2:
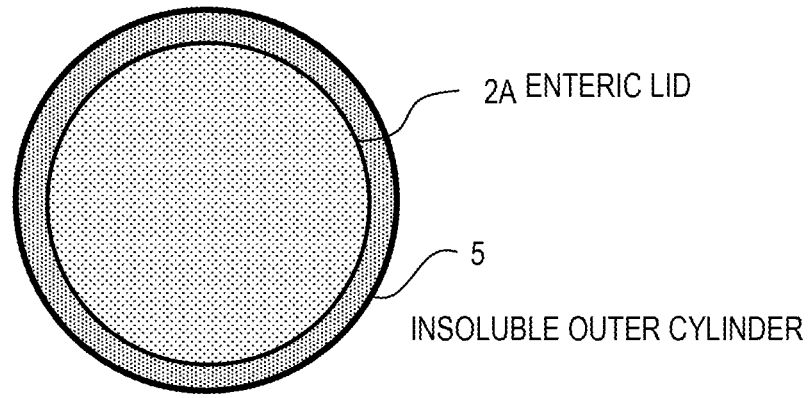
FIG. 2 shows a top view of the intestinal internal contents sampling capsule.

FIG. 2 shows a top view of the intestinal internal contents sampling capsule 1. According to the exemplary configuration shown in FIGS. 1 and 2, the enteric lids 2A and 2B have bowl-like shapes with U-shaped sections. The respective tips (on the opposite sides of the openings) of the enteric lids 2A and 2B are curved surfaces. The open-side ends of the enteric lids 2A and 2B are housed in the insoluble outer cylinder 5 and in tight contact with the inner surface of the insoluble outer cylinder 5. The enteric lids 2A and 2B compressed by the insoluble outer cylinder 5 exert elastic force to hold the enteric lids 2A and 2B on the insoluble outer cylinder 5. The open ends of the enteric lids 2A and 2B are in abutting contact with the open ends of the magnetic inner cylinder 4. By doing so, assembly of the intestinal internal contents sampling capsule is facilitated.

A different holding method is also applicable. For example, the enteric lids 2A and 2B may be fitted to the insoluble outer cylinder 5 in such a manner as to locate the enteric lids 2A and 2B external to the insoluble outer cylinder 5. Regarding the outer lid, a part of the outer lid may be made of an enteric material and the other part thereof may be made of an insoluble material. The enteric part dissolves in a small intestine and the outer lid is detached from the cylindrical container.

As shown in FIG. 1, the water-swellable lids 7A and 7B each corresponding to an inner lid are fixed with the threads 3A and 3B respectively to the magnetic inner cylinder 4 inside the enteric lids 2A and 2B. The water-swellable lids 7A and 7B occupy parts of the respective orifices (openings) of the magnetic inner cylinder 4, while the other parts of the orifices are left unblocked. According to the exemplary configuration shown in FIG. 1, the water-swellable lids 7A and 7B are separated from an inner wall surface of the magnetic inner cylinder 4 to form a clearance between the inner surface of the magnetic inner cylinder 4 and the outer side surface of each of the water-swellable lids 7A and 7B.

As will be described later, the marker material 6 flows out through the unblocked parts of the orifices, and intestinal internal contents flow into the magnetic inner cylinder 4 through these unblocked parts of the orifices. The water-swellable lids 7A and 7B swell in an intestine to enclose the orifices of the magnetic inner cylinder 4 in order to prevent outgoing flow of the housed intestinal internal contents. As a result of the presence of space around the water-swellable lids 7A and 7B, swelling of the water-swellable lids 7A and 7B becomes more effective in enclosing the orifices of the magnetic inner cylinder 4 in order to prevent outgoing flow of the intestinal internal contents.

Figure 3:
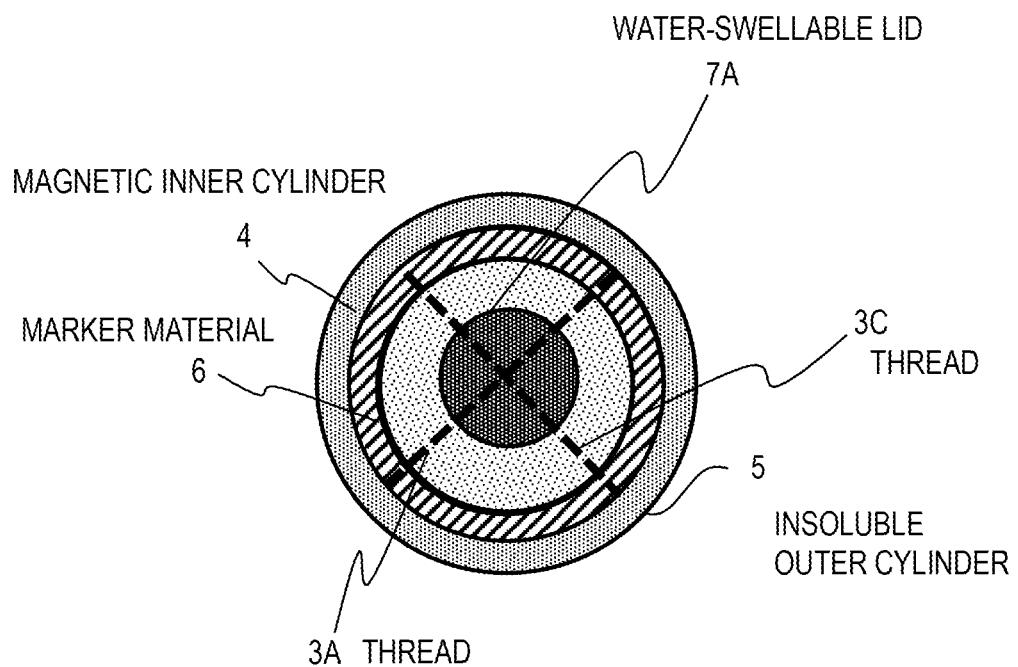
FIG. 3 is a sectional view taken in a radius direction of the intestinal internal contents sampling capsule.

FIG. 3 is a sectional view taken in a radius direction of the intestinal internal contents sampling capsule 1 (a radius direction vertical to an axis and corresponding to the right-to-left direction in FIG. 1). FIG. 3 shows the respective sections of the water-swellable lid 7A, the threads 3A, a thread 3C, and the magnetic inner cylinder 4 and the insoluble outer cylinder 5 housing the marker material 6.

As shown in FIGS. 1 and 3, the threads 3A and 3C penetrate the water-swellable lid 7A at different positions in the radius direction to be fixed to the magnetic inner cylinder 4. According to the exemplary configuration shown in FIG. 3, the threads 3A and 3C penetrate the water-swellable lid 7A in such a manner as to cross each other as viewed in an axis direction. The water-swellable lid 7A is not fixedly attached to the threads 3A and 3C but the threads 3A and 3C are slidable relative to the water-swellable lid 7A. According to a different exemplary configuration, the threads 3A and 3C may be parallel to each other as viewed in the axis direction. Likewise, the water-swellable lid 7B is fixed to the magnetic inner cylinder 4 using two threads including the thread 3B penetrating the water-swellable lid 7B.

As described above, fixing each of the water-swellable lids 7A and 7B using a plurality of threads penetrating each of the water-swellable lids 7A and 7B at different positions makes it possible to suppress the rotations of the water-swellable lids 7A and 7B. Each of the water-swellable lids 7A and 7B may be fixed with one thread, or the water-swellable lids 7A and 7B may be fixed with a different number of threads.

For example, the threads 3A, 3B, and 3C may be made of silk, polypropylene, polyester, or nylon, and may have a diameter from about 0.1 to about 1 mm. A thread-like part for fixing each of the water-swellable lids 7A and 7B is not limited to the threads shown in FIGS. 1 and 3. The thickness, sectional shape, and material of the thread-like part are determined freely. For example, a metallic wire may be used.

Each of the water-swellable lids 7A and 7B may be fixed to the cylindrical container without using the thread-like part. For example, a ring-like water-swellable lid may be fixed to the interior of the magnetic inner cylinder 4 in such a manner that the outer peripheral surface of the ring-like water-swellable lid tightly contacts the inner surface of the magnetic inner cylinder 4. The thread-like part may be fixed to the insoluble outer cylinder 5, and the water-swellable lid may swell to enclose the orifice of the insoluble outer cylinder 5.

Each of the water-swellable lids 7A and 7B is made of a water-swellable material and may be made using ethylene-vinyl acetate (EVA) or thermosetting elastomer, and water-absorbing polymer as a material. Each of the water-swellable lids 7A and 7B is made of any material allowing the water-swellable lids 7A and 7B to swell in response to contact with internal contents in a small intestine.

Each of the water-swellable lids 7A and 7B may have a columnar shape, for example. Each of the water-swellable lids 7A and 7B is arranged in such a manner that the axis thereof extends parallel to the axis of the magnetic inner cylinder 4. By doing so, the orifices of the magnetic inner cylinder 4 can be enclosed by causing the water-swellable lids 7A and 7B to swell appropriately. The sectional shape of each of the water-swellable lids 7A and 7B may be a columnar shape such as a circular column, for example, similar to the shape of the orifices of the magnetic inner cylinder 4. By doing so, it becomes possible to enclose the orifices of the magnetic inner cylinder 4 more reliably in response to swelling of the water-swellable lids 7A and 7B.

The thickness of each of the water-swellable lids 7A and 7B (length in the axis direction) may be less than the diameter thereof before and after swelling. Setting a maximum size of the water-swellable lid in the axis direction to be less than a maximum size thereof in the radius direction before and after swelling makes it possible to alleviate reduction in housing space for housing intestinal internal contents to be caused by the swelling. For example, each of the water-swellable lids 7A and 7B may be a circular column of a diameter from about 3 to 4 mm and a thickness from about 1.5 to 2 mm. According to a different exemplary configuration, the water-swellable lid may be a spherical body and may be supported using only one thread-like part. If an opening is formed only on one side of the magnetic inner cylinder 4 and the magnetic inner cylinder 4 is closed on the other side, the water-swellable lid is arranged only on the open side.

As shown in FIG. 1, the marker material 6 is housed in advance in the intestinal internal contents sampling capsule 1. The marker material 6 is a powder and granular material. This makes it possible to prevent the water-swellable lids 7A and 7B housed in the cylindrical container from being caused to swell by the marker material 6.

As will be described later, the marker material 6 flows out through the clearance between each of the water-swellable lids 7A and 7B and the inner surface of the magnetic inner cylinder 4 in an intestine, and is then discharged in feces together with the intestinal internal contents sampling capsule 1. The marker material 6 may be any material insoluble in an intestine and easily recognizable from around the marker material 6 in feces. The marker material 6 may be a coloring matter such as melanin from squid ink or tiny seeds of sesame, kiwis, or strawberries, for example. According to one example, the marker material 6 is an edible marker material. This makes it possible to avoid influence on a test subject more reliably.

Figure 4:
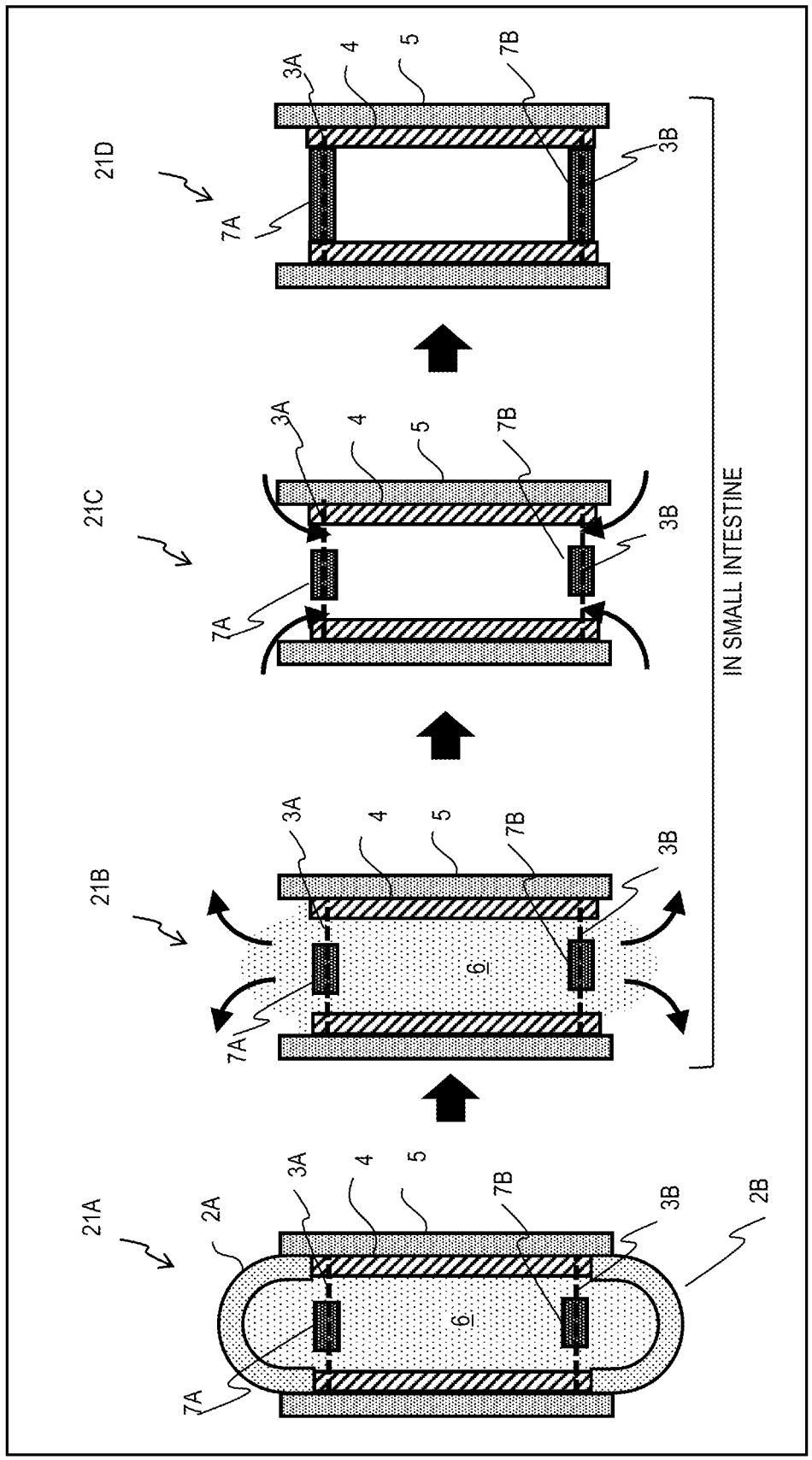
FIG. 4 schematically shows the operation of the swallowed intestinal internal contents sampling capsule.

A method of sampling intestinal internal contents using the intestinal internal contents sampling capsule 1 will be described next. FIG. 4 schematically shows the operation of the swallowed intestinal internal contents sampling capsule 1. In a state 21A before being swallowed, the intestinal internal contents sampling capsule 1 has the configuration described by referring to FIGS. 1 to 3.

After being swallowed by a test subject, the intestinal internal contents sampling capsule 1 passes through a gullet and a stomach to reach a small intestine. In the small intestine, the intestinal internal contents sampling capsule 1 changes from the state 21A to a state 21B. More specifically, each of the enteric lids 2A and 2B partially dissolves to be detached from the insoluble outer cylinder 5. Then, the orifices of each of the insoluble outer cylinder 5 and the magnetic inner cylinder 4 are exposed to cause the marker material 6 housed therein to flow out through the orifice between each of the water-swellable lids 7A and 7B and the magnetic inner cylinder 4.

In the small intestine, the intestinal internal contents sampling capsule 1 changes further from the state 21B to a state 21C. More specifically, intestinal internal contents pass through the orifice between each of the water-swellable lids 7A and 7B and the magnetic inner cylinder 4 to flow into the intestinal internal contents sampling capsule 1. The presence of the orifices on the both sides of each of the insoluble outer cylinder 5 and the magnetic inner cylinder 4 achieves efficient outgoing flow of the marker material 6 and efficient incoming flow of the intestinal internal contents.

In the small intestine, the intestinal internal contents sampling capsule 1 changes further from the state 21C to a state 21D. More specifically, the water-swellable lids 7A and 7B swell to enclose the orifices on the both sides of the magnetic inner cylinder 4. Each of the water-swellable lids 7A and 7B swells in such a manner as to slide on the threads penetrating each of the water-swellable lids 7A and 7B in the radius direction, and the threads remain stretched.

The intestinal internal contents are housed in the enclosed space. The intestinal internal contents sampling capsule 1 in the state 21D thereafter goes from the small intestine and passes through a large intestine, and is then discharged together with feces. The marker material 6 having flowed out is also discharged together with the intestinal internal contents sampling capsule 1 and the feces.

A position of sampling internal contents in a small intestine becomes controllable by adjusting the thickness of each of the enteric lids 2A and 2B and changing time of dissolving correspondingly, for example. A duration of sampling time becomes controllable by designing a material composition of the water-swellable lid and changing a swelling rate correspondingly.

Figure 5:
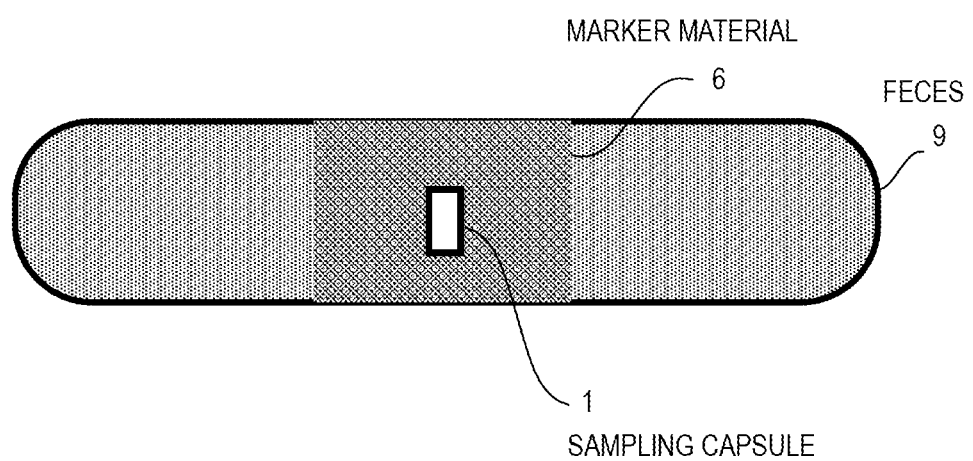
FIG. 5 schematically shows an intestinal internal contents sampling capsule 1 and a marker material discharged together with feces.

FIG. 5 schematically shows the intestinal internal contents sampling capsule 1 and the marker material 6 discharged together with feces. After flowing out from the intestinal internal contents sampling capsule 1, the marker material 6 exists mainly around the intestinal internal contents sampling capsule 1 in feces 9. As described above, the marker material 6 exhibits a different appearance from surrounding usual feces in terms of a different color or texture, for example. The presence of the marker material 6 allows a tester to estimate the position of the intestinal internal contents sampling capsule 1 easily.

Figure 6:
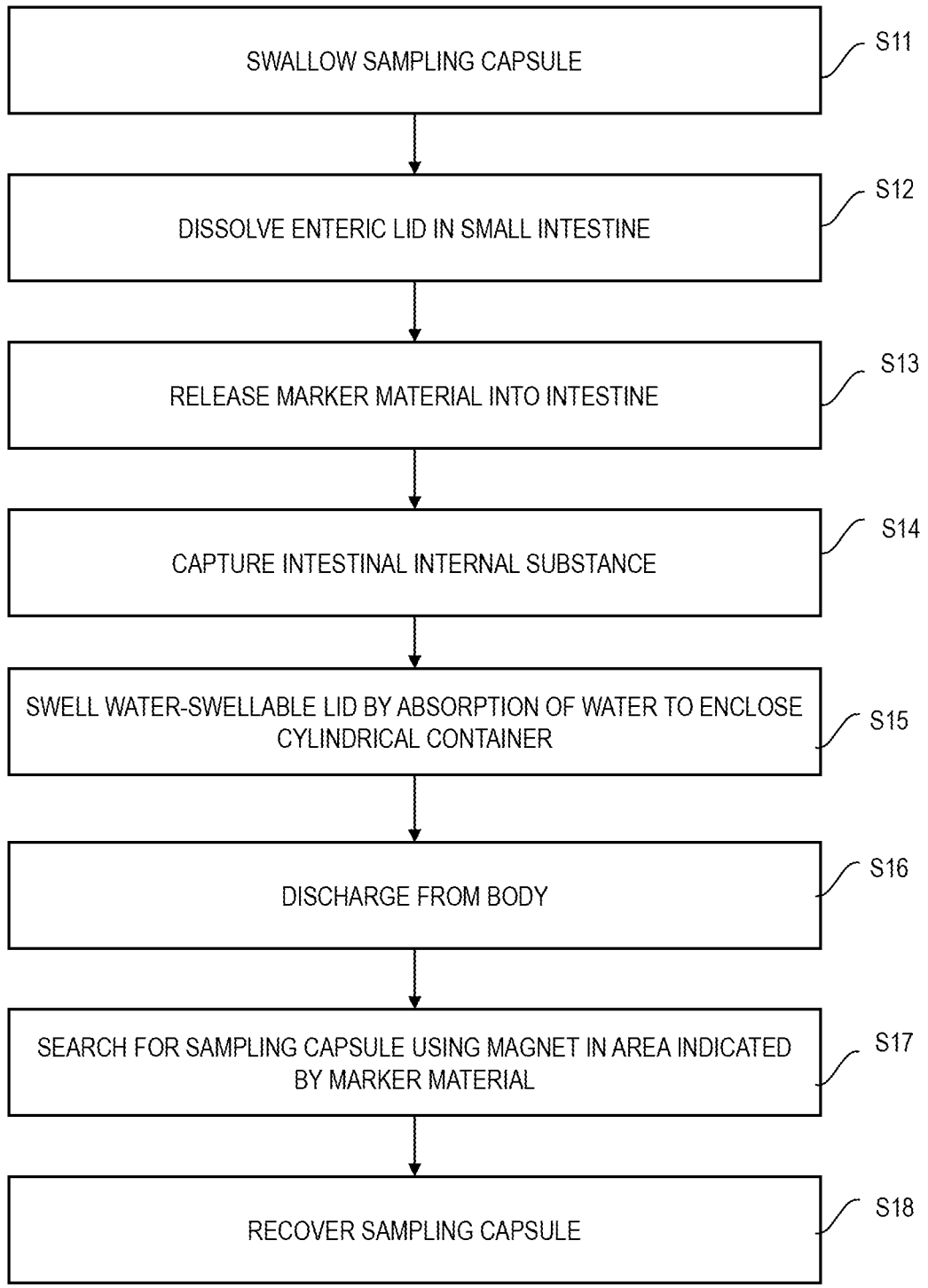
FIG. 6 shows a flow from swallowing of the intestinal internal contents sampling capsule by a test subject to recovery of the intestinal internal contents sampling capsule 1 from feces by a tester.

A flow from swallowing of the intestinal internal contents sampling capsule 1 by a test subject to recovery of the intestinal internal contents sampling capsule 1 from feces by a tester will be described next by referring to the flowchart of FIG. 6 and the state transition view of FIG. 4. First, the test subject swallows the intestinal internal contents sampling capsule 1 having the configuration shown in FIG. 1 from a mouth (S11 and the state 21A in FIG. 4). The intestinal internal contents sampling capsule 1 passes through a gullet and a stomach to reach a small intestine.

In the small intestine, the enteric lids 2A and 2B dissolve to open the enclosed insoluble outer cylinder 5 and the magnetic inner cylinder 4 (S12 and the state 21B in FIG. 4). The marker material 6 housed in the insoluble outer cylinder 5 and the magnetic inner cylinder 4 is released into the intestine (S13 and the state 21B in FIG. 4).

Internal contents in the small intestine are captured into the internal spaces of the insoluble outer cylinder 5 and the magnetic inner cylinder 4 (S14 and the state 21C in FIG. 4). The water-swellable lids 7A and 7B absorb water in the small intestine to swell gradually and slowly over time, thereby enclosing the magnetic inner cylinder 4 (S15 and the state 21C in FIG. 4). The internal contents in the small intestine is housed in the enclosed space. The intestinal internal contents sampling capsule 1 housing the internal contents in the small intestine and the released marker material 6 are discharged from a body together with feces (S16).

As described above by referring to FIG. 5, the marker material 6 is a rough indication of the position of the intestinal internal contents sampling capsule 1 in feces. The tester inserts a magnet into an area indicated by the marker material and searches for the intestinal internal contents sampling capsule 1 (S17). Using the magnet allows more efficient search of the intestinal internal contents sampling capsule 1 in the feces. The magnetic inner cylinder 4 is attracted to the magnet to attach the intestinal internal contents sampling capsule 1 to the magnet. The tester recovers the intestinal internal contents sampling capsule 1 by detaching the intestinal internal contents sampling capsule 1 from the magnet (S18).

Figure 7A:
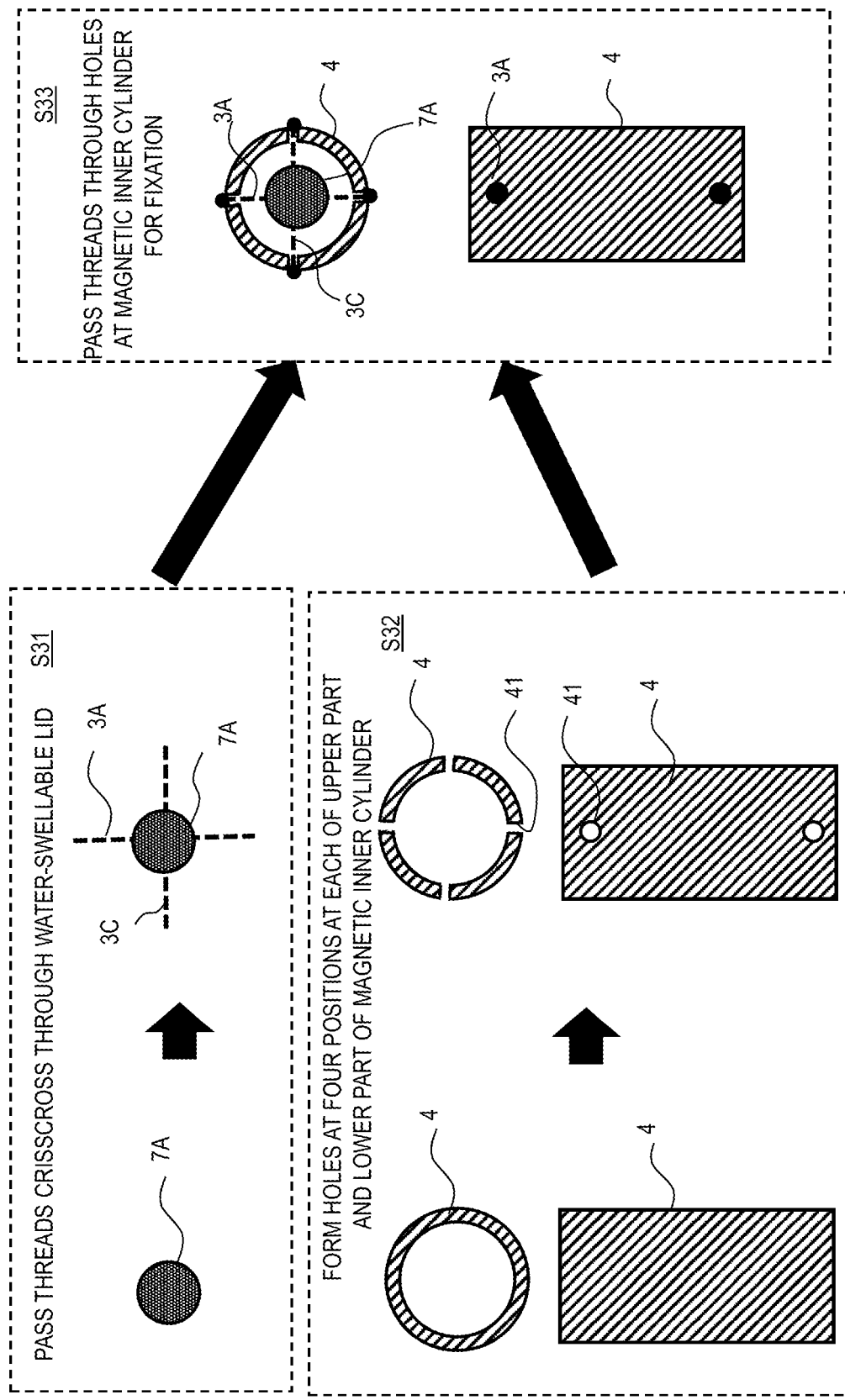
FIGS. 7A to 7C schematically show an exemplary method of preparing the intestinal internal contents sampling capsule.
Figure 7B:
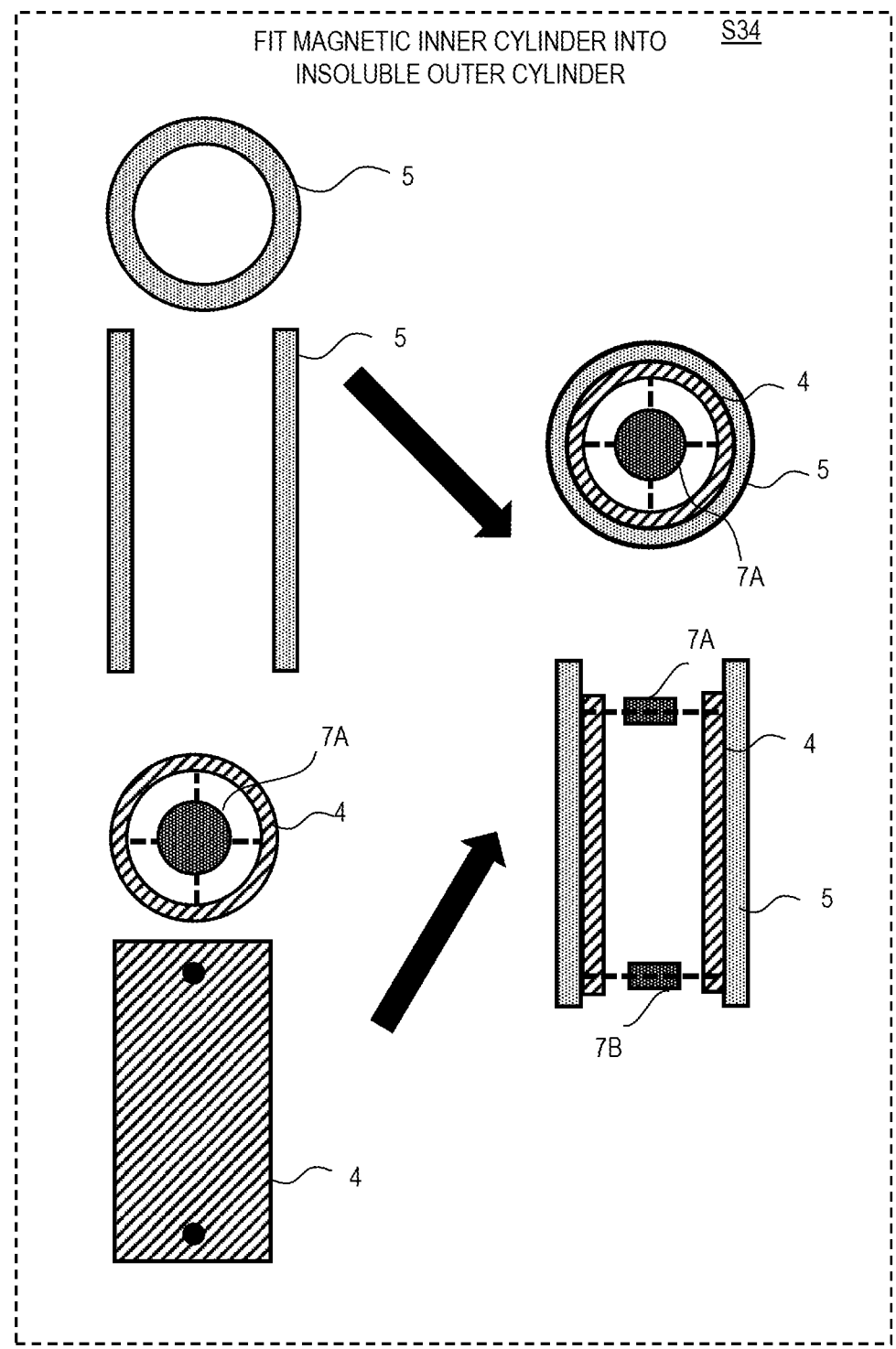
Figure 7C:
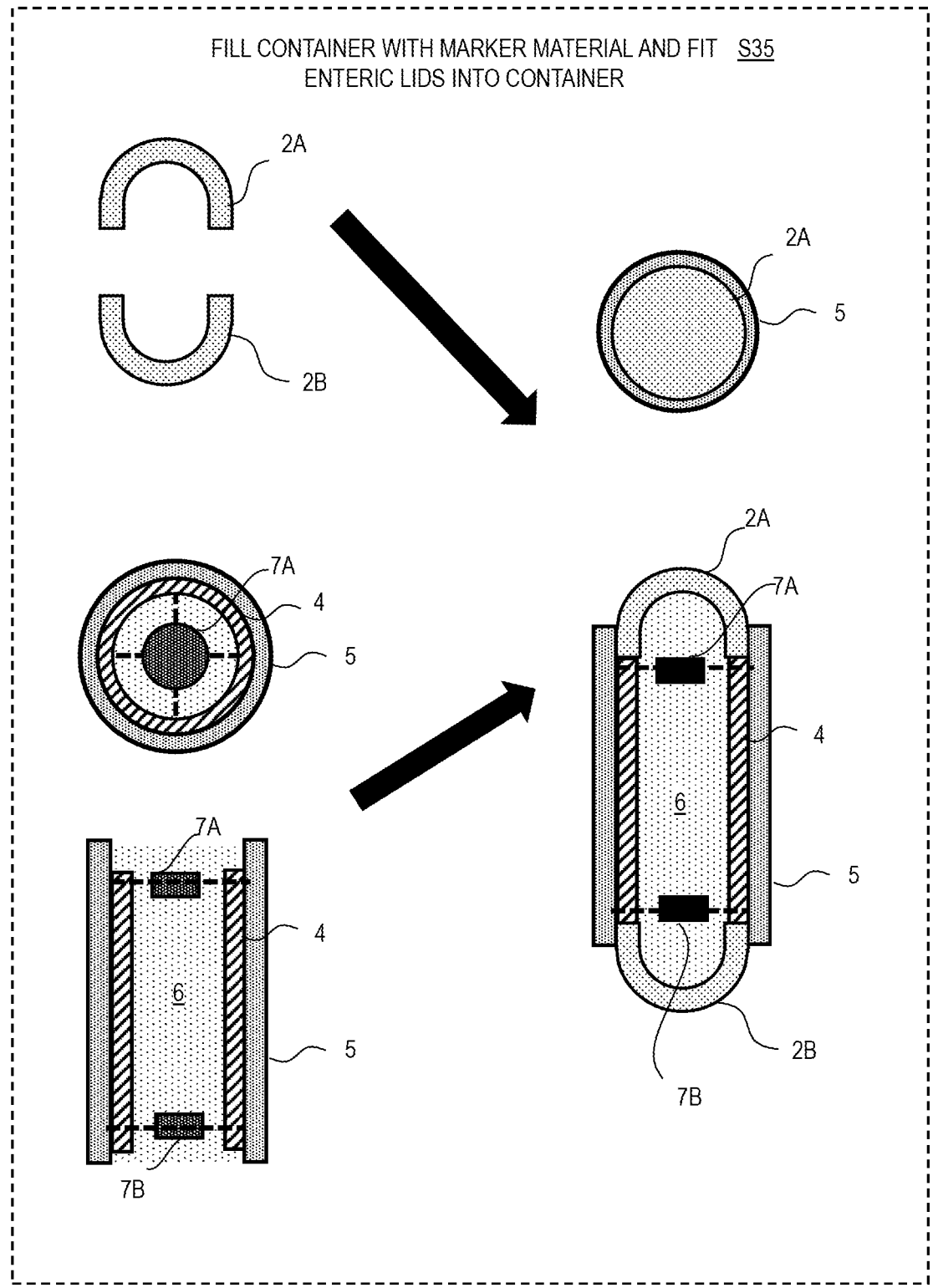

The following describes a method of preparing the intestinal internal contents sampling capsule 1. FIGS. 7A to 7C schematically show an exemplary method of preparing the intestinal internal contents sampling capsule 1. By referring to FIG. 7A, according to the preparation method, two threads are passed through each of the water-swellable lids 7A and 7B (S31). As an example, FIG. 7A shows a top view of the water-swellable lid 7A with the threads 3A and 3C penetrating the water-swellable lid 7A. The threads are passed in such a manner as to cross each other in the radius direction of the water-swellable lid having a circular columnar shape (directions vertical to the axis direction). In the example shown in FIG. 7A, the threads 3A and 3C are at a right angle. Two threads are passed in a similar manner through the water-swellable lid 7B.

According to the preparation method, four holes 41 are further formed at each of an upper part and a lower part of the magnetic inner cylinder 4 (S32). FIG. 7A shows a top view and a side view of the magnetic inner cylinder 4 before formation of the holes, and a top view and a side view of the magnetic inner cylinder 4 after formation of the holes. In FIG. 7A, one hole designated by a sign 41 is shown as an example. The four holes are at the same position as viewed in the axis direction. Adjacent holes are at an angle of 90° relative to each other as viewed in the axis direction. The threads penetrating each of the water-swellable lids 7A and 7B are passed through these holes.

Next, according to the preparation method, the threads penetrating each of the water-swellable lids 7A and 7B are passed through the holes 41 at the magnetic inner cylinder 4 for fixation (S33). FIG. 7A shows a top view and a side view of the magnetic inner cylinder 4 to which the water-swellable lids 7A and 7B are fixed. A knot may be formed at an end of each thread, or a different fixing method is applicable. Fixing the threads to the holes formed at the magnetic inner cylinder 4 not at the insoluble outer cylinder 5 makes it possible to prevent incoming and outgoing flows of liquid through the holes more reliably.

By referring to FIG. 7B, the magnetic inner cylinder 4 with the attached water-swellable lids 7A and 7B is thereafter fitted into the insoluble outer cylinder 5 (S34). FIG. 7B shows a top view and a side view of each of the insoluble outer cylinder 5 and the magnetic inner cylinder 4 before being combined together. FIG. 7B further shows a top view and a side view of each of the insoluble outer cylinder 5 and the magnetic inner cylinder 4 after being combined together.

By referring to FIG. 7C, the combination of the insoluble outer cylinder 5 and the magnetic inner cylinder 4 is thereafter filled with the marker material 6. Then, the enteric lids 2A and 2B are fitted into the combination of the insoluble outer cylinder 5 and the magnetic inner cylinder 4 housing the marker material 6 (S35). The enteric lids 2A and 2B are fitted to the interior of the insoluble outer cylinder 5. FIG. 7C shows a side view of each of the enteric lids 2A and 2B, and a top view and a side view of the combination of the insoluble outer cylinder 5 and the magnetic inner cylinder 4 housing the marker material 6. FIG. 7C further shows a top view and a side view of the combination of the insoluble outer cylinder 5 and the magnetic inner cylinder 4 housing the marker material 6 and including the fitted enteric lids 2A and 2B.

As described above, according to this embodiment, for recovery of the sampling capsule from feces after the sampling capsule is discharged from a body, the sampling capsule can be searched for using an area indicated by the marker as a target having flowed out of the sampling capsule.

Second Embodiment

Figure 8:
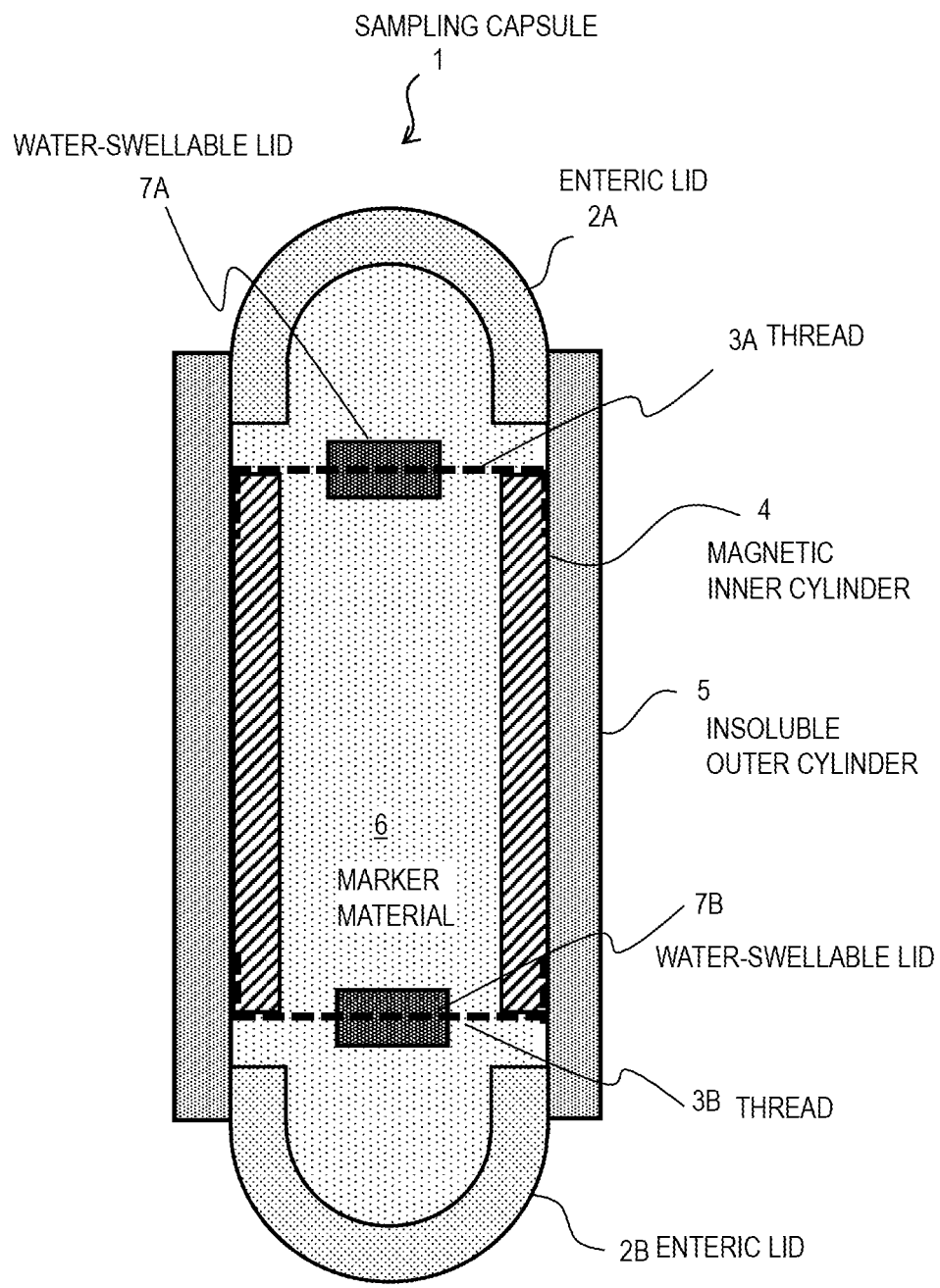
FIG. 8 shows an exemplary configuration of an intestinal internal contents sampling capsule according to a second embodiment.

A different embodiment will be described below. The following description is mainly intended for a difference from the exemplary configuration shown in the first embodiment. FIG. 8 shows a different exemplary configuration of the intestinal internal contents sampling capsule 1. According to this exemplary configuration, both ends of each of the threads 3A and 3B penetrating the water-swellable lids 7A and 7B respectively are interposed between the magnetic inner cylinder 4 and the insoluble outer cylinder 5. Likewise, the other threads not shown in the drawings penetrating the water-swellable lids 7A and 7B are interposed at their ends between the magnetic inner cylinder 4 and the insoluble outer cylinder 5. Fixing the threads to the cylindrical container in this way allows the intestinal internal contents sampling capsule 1 to be assembled more easily.

According to the exemplary configuration shown in FIG. 8, the threads 3A and 3B enter a gap between the magnetic inner cylinder 4 and the insoluble outer cylinder 5 from upper and lower ends of the magnetic inner cylinder 4 respectively without being passed through the holes formed at the magnetic inner cylinder 4. This also applies to the other threads not shown in the drawings penetrating the water-swellable lids 7A and 7B. By doing so, the need of forming the holes at the magnetic inner cylinder 4 is eliminated.

According to the exemplary configuration described in the first embodiment, the marker material 6 is a powder and granular material housed in advance in the cylindrical container. According to a different exemplary configuration, the marker material may be a fluorescent material contained in a material of a fixed part of the intestinal internal contents sampling capsule 1. The fluorescent material emits light in a specific color in response to light coming from outside such as an ultraviolet ray or visible light. As the fluorescent material, a material containing indocyanine green (ICG) is applicable, for example. The fluorescent material may be contained in a material of the insoluble outer cylinder 5 or may be contained in a material of a different fixed part.

Figure 9:
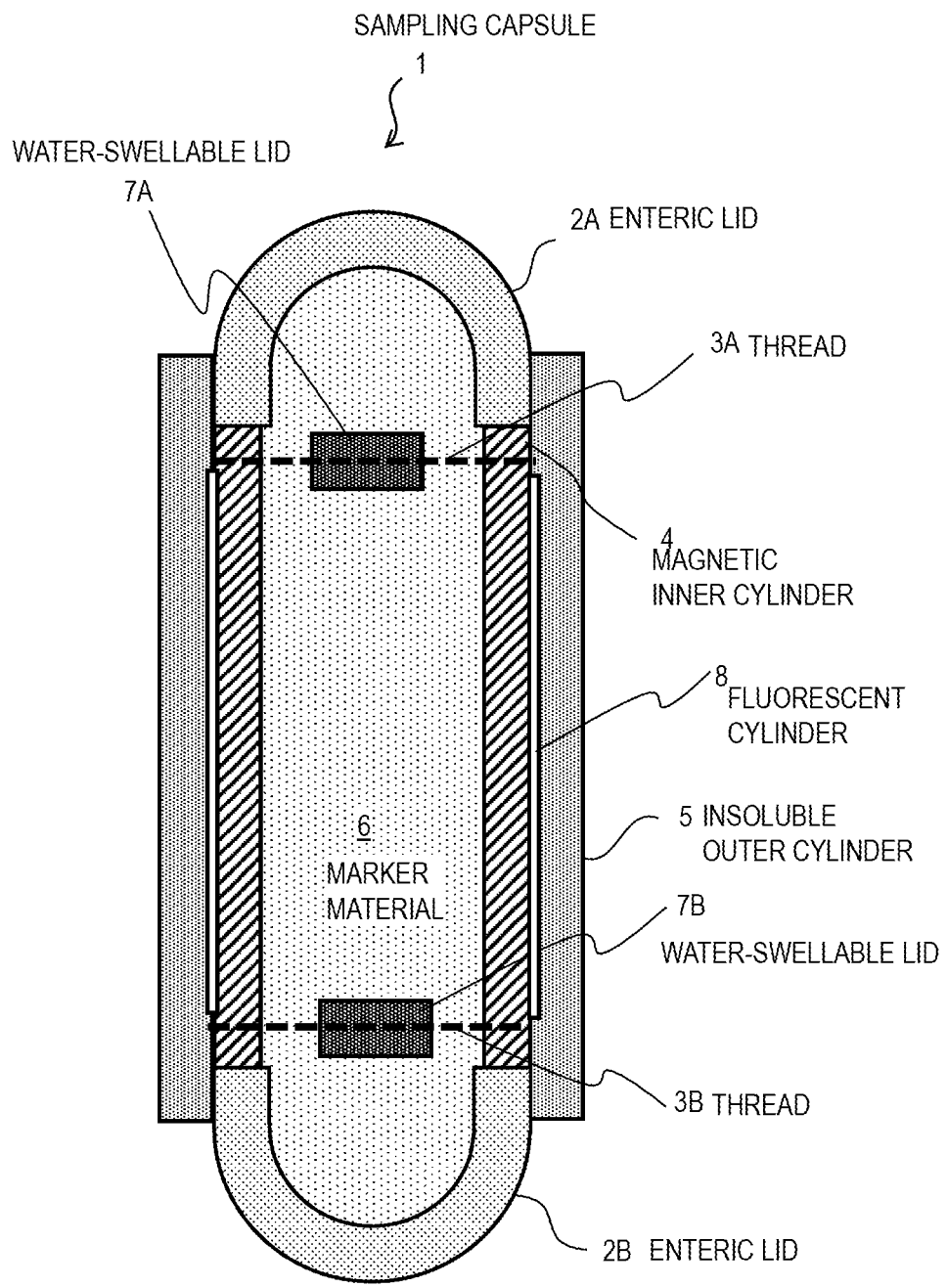
FIG. 9 shows a different exemplary configuration of an intestinal internal contents sampling capsule including a fixed part containing a fluorescent material.

FIG. 9 shows a different exemplary configuration of the intestinal internal contents sampling capsule 1 including a fixed part containing a fluorescent material. The exemplary configuration shown in FIG. 9 includes a fluorescent cylinder 8 interposed between the insoluble outer cylinder 5 and the magnetic inner cylinder 4, in addition to the exemplary configuration of the intestinal internal contents sampling capsule 1 shown in FIG. 1. The fluorescent cylinder 8 is an insoluble fluorescent part made of a material containing a fluorescent material. The fluorescent cylinder 8 may be made of silicon in which the fluorescent material is mixed, for example. Interposing the fluorescent part between the insoluble outer cylinder 5 and the magnetic inner cylinder 4 in this way makes it possible to avoid influence on a digestive tract that may be caused by exposure of the fluorescent part to the interior of the digestive tract.

Figure 10:
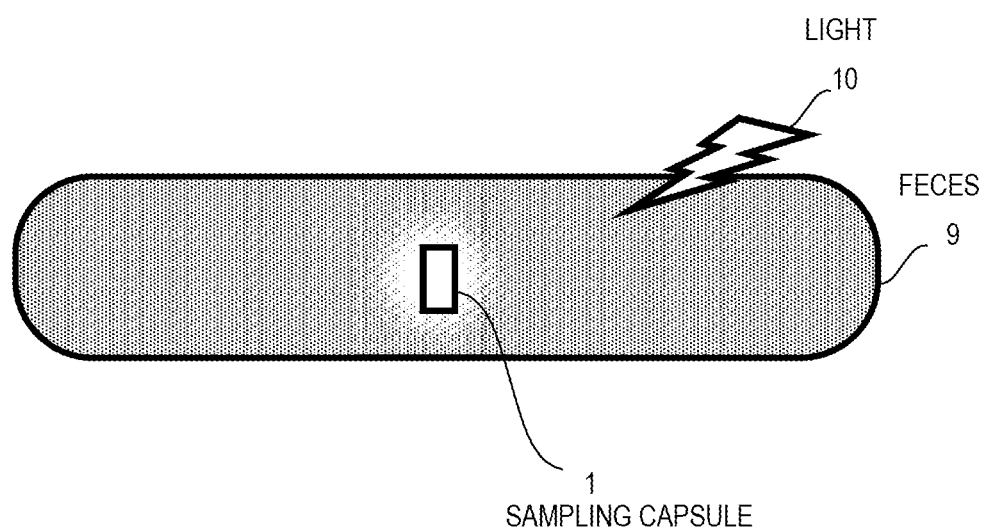
FIG. 10 schematically shows the intestinal internal contents sampling capsule containing the fluorescent material discharged together with feces.

FIG. 10 schematically shows the intestinal internal contents sampling capsule 1 containing the fluorescent material discharged together with feces. In response to application of light 10 of a predetermined wavelength range, the fluorescent material in the intestinal internal contents sampling capsule 1 emits light. The fluorescent light from the intestinal internal contents sampling capsule 1 allows a tester to estimate the position of the intestinal internal contents sampling capsule 1 easily.

The present invention is not to be limited to the foregoing embodiments but it includes various modifications. For example, while the foregoing embodiments have been described in detail for better understanding of the present invention, the present invention is not always limited to a configuration including all the structures in the description. Additionally, a part of a structure in one embodiment can be replaced with a structure in a different embodiment, and a structure in one embodiment can be added to a structure in a different embodiment. Further, a part of a structure in each embodiment can be subjected to addition by a different structure, deletion, or replacement with a different structure.

What is claimed is:

1. A digestive organ internal contents sampling capsule for sampling internal contents in a digestive organ, comprising:
   a cylindrical container insoluble in a digestive tract for housing the internal contents in the digestive organ, the cylindrical container including an inner cylinder and an outer cylinder;
   an outer lid enclosing an orifice of the cylindrical container and the outer lid is configured to dissolve at least partially in the digestive organ;
   an inner lid arranged in the cylindrical container, and the inner lid is configured to swell in response to contact with the internal contents in the digestive organ to enclose the orifice of the cylindrical container after the orifice is exposed by dissolving of at least a part of the outer lid; and
   a marker material to be discharged together with the cylindrical container housing the internal contents in the digestive organ and feces;
   wherein the inner cylinder abuts an open end of the outer lid, and the outer cylinder extends axially beyond a location where the inner cylinder abuts the open end of the outer lid, such that the outer cylinder overlaps the outer lid in an axial direction of the digestive organ internal contents sampling capsule.

2. The digestive organ internal contents sampling capsule according to claim 1, wherein
   the marker material is housed in advance in the cylindrical container and is caused to flow out from the cylindrical container by dissolving of at least a part of the outer lid.

3. The digestive organ internal contents sampling capsule according to claim 2, wherein
   the inner lid is made of a water-swellable material, and the marker material is a powder and granular material.

4. The digestive organ internal contents sampling capsule according to claim 2, wherein
   the marker material is an edible material.

5. The digestive organ internal contents sampling capsule according to claim 1, wherein
   the marker material is a fluorescent material contained in a material forming the cylindrical container.

6. The digestive organ internal contents sampling capsule according to claim 1, wherein
   the marker material is a fluorescent material, and
   the fluorescent material is contained in a part interposed between the inner cylinder and the outer cylinder.

7. The digestive organ internal contents sampling capsule according to claim 1, wherein
   the inner cylinder is made of a magnetic material.

8. The digestive organ internal contents sampling capsule according to claim 1, wherein
   the outer lid is a first outer lid, and
   the inner lid is a first inner lid,
   the digestive organ internal contents sampling capsule further comprising:
   a second outer lid enclosing an orifice of the cylindrical container on an opposite side of the first outer lid and the second outer lid is configured to dissolve at least partially in the digestive organ; and
   a second inner lid arranged in the cylindrical container, and the second inner lid is configured to swell in response to contact with the internal contents in the digestive organ to enclose the orifice of the cylindrical container after the orifice is exposed by dissolving of at least a part of the second outer lid.

9. The digestive organ internal contents sampling capsule according to claim 1, further comprising:
   a thread-like part penetrating the inner lid and fixed to the cylindrical container, wherein
   the inner lid is separated from an inner wall surface of the cylindrical container before the inner lid swells.

10. The digestive organ internal contents sampling capsule according to claim 9, further comprising:
    a plurality of thread-like parts penetrating the inner lid at different positions and fixed to the cylindrical container, wherein
    the inner lid supported by the thread-like parts has a maximum size as viewed in an axis direction of the cylindrical container less than a maximum size of the inner lid as viewed in a radius direction of the cylindrical container before and after swelling of the inner lid.

11. The digestive organ internal contents sampling capsule according to claim 9, wherein
    both ends of the thread-like part are fixed to the inner cylinder.

12. The digestive organ internal contents sampling capsule according to claim 9, wherein
    both ends of the thread-like part are interposed between the inner cylinder and the outer cylinder.

13. The digestive organ internal contents sampling capsule according to claim 1, wherein
    the inner cylinder has higher rigidity than the outer cylinder.

14. The digestive organ internal contents sampling capsule according to claim 1, wherein
    the digestive organ is a small intestine.

* * * * *